US010763565B1

(12) United States Patent
Green

(10) Patent No.: US 10,763,565 B1
(45) Date of Patent: Sep. 1, 2020

(54) PULSED ELECTROMAGNETIC FIELD THERAPY SYSTEM AND METHOD

(71) Applicant: Ronald Patrick Green, San Jose, CA (US)

(72) Inventor: Ronald Patrick Green, San Jose, CA (US)

(*) Notice: Subject to any disclaimer, the term of this patent is extended or adjusted under 35 U.S.C. 154(b) by 133 days.

(21) Appl. No.: 16/016,363

(22) Filed: Jun. 22, 2018

(51) Int. Cl.
*A61N 2/02* (2006.01)
*A61N 1/00* (2006.01)
*A61N 2/00* (2006.01)
*H01P 3/08* (2006.01)
*H05K 1/02* (2006.01)
*A61N 1/40* (2006.01)

(52) U.S. Cl.
CPC ............... *H01P 3/08* (2013.01); *A61N 1/40* (2013.01); *H05K 1/0237* (2013.01); *H05K 1/0256* (2013.01); *H05K 2201/0154* (2013.01); *H05K 2201/093* (2013.01); *H05K 2201/09263* (2013.01)

(58) Field of Classification Search
CPC ...... C12N 15/87; C12N 13/00; A61N 1/0412; A61N 1/327; A61N 2/00; A61N 2/02; A61N 2/008; C12M 35/02; A61K 48/00
See application file for complete search history.

(56) References Cited

U.S. PATENT DOCUMENTS

| 6,443,883 B1 | 9/2002 | Ostrow et al. |
| 8,822,222 B2 | 9/2014 | Bebe et al. |
| 2014/0008119 A1* | 1/2014 | Brandt ................. H05K 9/0073 174/382 |

OTHER PUBLICATIONS

Romeo S., et. al., "Modified Blumlein Pulse-Forming Networks for Bioelectrical Applications", Journal of Membrane Biology Jul. 7, 2010, DOI: 10.1007/s00232-010-9273-2.

* cited by examiner

*Primary Examiner* — Jon Eric C Morales
(74) *Attorney, Agent, or Firm* — Stephen E. Zweig

(57) ABSTRACT

System and method of applying pulsed electromagnetic fields (PEMF) to a human user's body. Here an electrically isolated antenna is applied to a portion of the body. This antenna is connected to a PEMF power source comprising a modified Blumlein dual transmission line transformer circuit with emphasis on miniaturization. Each transmission line comprises a substantially planar PC board mounted conducting strip configured in a meander pattern, and separated from at least one split ground plane by at least one substantially planar dielectric material and at least one split ground plane. This in turn is powered by a low voltage power supply, resonant transformer. The Blumlein circuit is charged and discharged by a processor controlled high-speed switch according to user selected time settings, and can produce outputs substantially above 1 kV. Relative to prior art devices, the system enables much smaller, lighter, and less costly PEMF implementations.

20 Claims, 13 Drawing Sheets

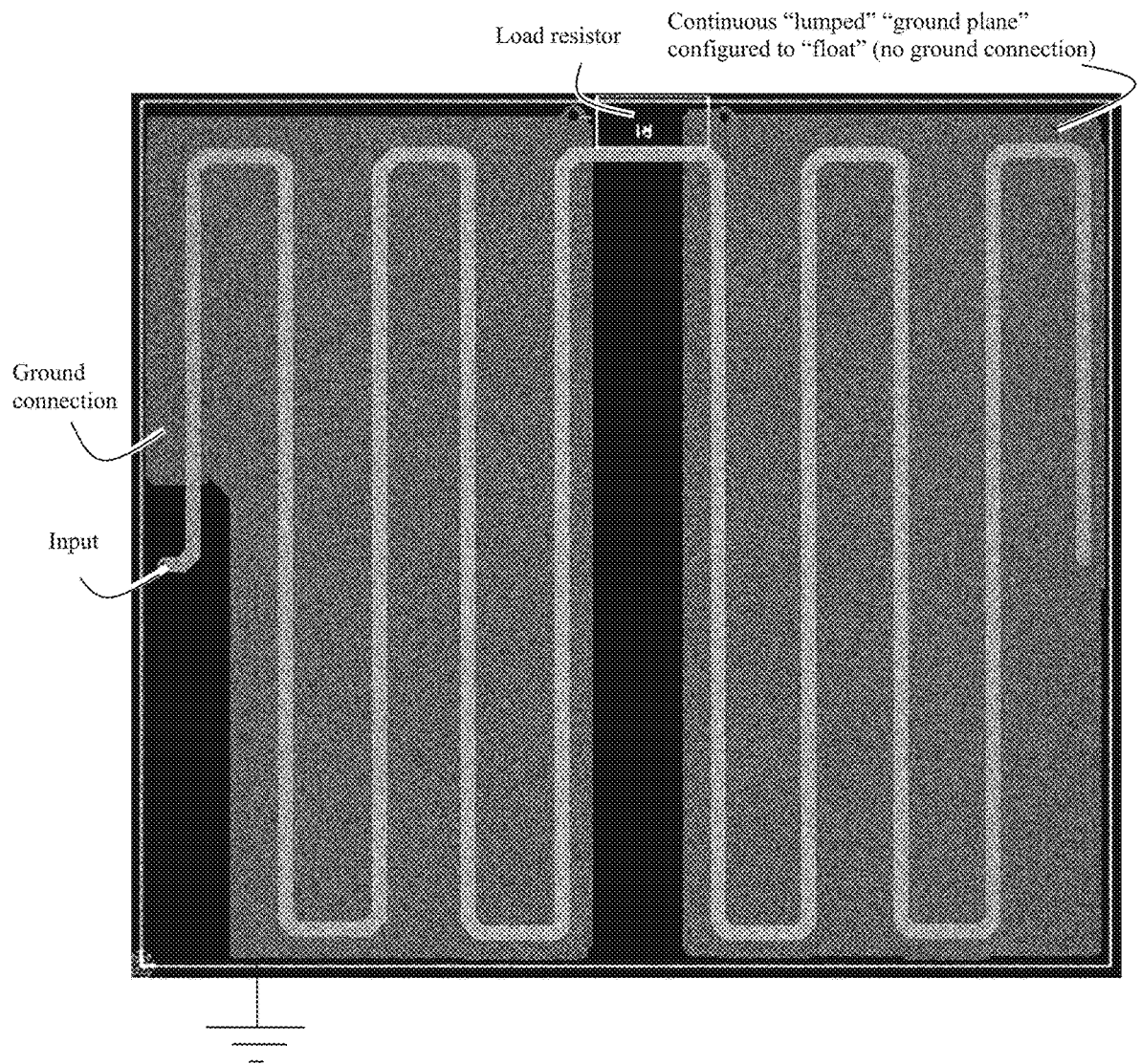

PULSED ELECTROMAGNETIC FIELD THERAPY SYSTEM AND METHOD

BACKGROUND OF THE INVENTION

Field of the Invention

This invention is in the field of systems, methods, and devices suitable for pulsed electromagnetic field (PEMF) therapy.

Description of the Related Art

Although electromagnetic field therapy has been known for many years, in recent years, an alternative type of electromagnetic field therapy, called "pulsed electromagnetic field therapy", or "PEMF", as applied to various portions of a human user's body, has received increasing interest. Certain types of PEMF therapy are known to be beneficial to help promote the healing of broken bones, and certain types have received FDA approval indications such as cervical fusion surgery.

Although, for human use purposes, PEMF devices and methods sold with specific health claims require FDA clearance, use of PEMF devices and methods sold without specific health claims are also marketed. For example, high energy PEMF systems for human users, which produce outputs in excess of 1 kilovolt (kV), are presently marketed by Pulse Centers as PEMF exercise systems.

Examples of such prior art systems include Bebe et. al., U.S. Pat. No. 8,822,222, and other patents. As per Bebe and other type systems, one popular method that produces suitable brief electromagnetic pulses is to employ systems and methods that use dual-line Blumlein transmission line coaxial circuits, described in Blumlein, U.S. Pat. No. 2,496,979. An example of a prior art Blumlein transmission circuit is shown in FIG. 1. Such Blumlein circuits are described in more detail in chapter 13.2.10 by J. E. Dolan in "Advances in High Voltage Engineering, Haddad and Warne Editors, 2004 by the Institute of engineering and technology, London UK.

Operation of Blumlein transformer circuits: to paraphrase somewhat from the Wikipedia article on pulse forming networks (https://en.wikipedia.org/wiki/Pulse_forming_network), in a Blumlein circuit, to trigger the pulse, a switch short-circuits the line at the power supply end, causing a negative voltage step to travel toward the load. Since the characteristic impedance $Z_0$ of the line is made equal to half the load impedance $R_L$, the voltage step is half reflected and half transmitted, resulting in two symmetrical opposite polarity voltage steps which propagate away from the load, creating between them a voltage drop of V/2−(−V/2)=V across the load. The voltage steps reflect from the ends and return, ending the pulse. As in other charge line generators, the pulse duration is equal to 2D/c, where D is the length of the individual transmission lines, and c is the speed of the transmission line pulse (usually a significant fraction of the speed of light).

Romeo et. al., "Modified Blumlein Pulse-Forming Networks for Bioelectrical Applications", J. Membrane Biol. Jul. 9, 2010, DOI 10.1007/s00232-010-9273-2 taught a regular microstrip line modified Blumlein pulse forming network. However the amplitude of the pulses generally appears to be limited to about 1 kilovolt (kV). This is a low power device primarily intended for applying pulsed electrical fields directly to isolated cell suspensions on microscopic slides, often between electrodes separated by a gap of only 100 µm.

PEMF methods are also presently being investigated for many other medical and non-medical therapeutic indications, including pain relief, depression, healing, other bone repair indications, improvements in blood circulation, and other uses.

BRIEF SUMMARY OF THE INVENTION

The invention is based, in part on the insight that prior art Blumlein transmission line/transformer type PEMF devices intended for human use, such as the previously discussed pulse centers methods, use rather massive, large and unwieldy coaxial cables in order to implement their Blumlein circuitry. Thus improved PEMF devices, that can implement Blumlein pulse generation methods with smaller, more portable, and less expensive methods that avoid the use of such coaxial cables would be useful.

Although some workers, such as Romeo et. al., have attempted to reduce the size of Blumlein devices by using regular microstrip designs implemented on printed circuit boards, these systems were not intended for human users. In the Romeo system, as previously discussed, the amplitude of the pulses was limited to about 1 kilovolt (kV). This device was a low power device designed to apply pulsed electrical fields directly to isolated cell suspensions on microscopic slides, using electrode gaps of only 100 µm. Generally these voltage levels appear to be too low provide much benefit for human use, and such electrode configurations would be entirely unsuitable for human use.

The present invention is also based, in part, on the insight that by using improved printed circuit designs, such improved PEMF devices and systems, configured to deliver pulses with amplitudes considerably above 1 kV, and suitable for safer and more feasible pulse delivery options, could be created by implementing Blumlein transmission line/ circuits using less bulky planar transmission lines and split ground plane techniques, which in turn can be implemented using lower cost and smaller printed circuit board technology.

The invention is also based, in part, on the insight in a preferred embodiment, such improved PEMF devices may further employ additional devices and methods. These additional devices and methods can include use of low voltage (e.g. 12-volt) power supplies, use of resonant transformers to step up the voltage, and improved Blumlein circuits based on meander type printed circuit transmission lines, as well as split ground plane designs that further incorporate floating ground plane methods.

Thus, as will be described, in some embodiments the invention may be a pulsed electromagnetic field (PEMF) therapy system. This system will typically comprise a Blumlein transformer circuit type PEMF power source enclosed in a housing (e.g. a case). This Blumlein circuit will typically be connected in connected in series between two, equal length, substantially planar conducting strip transmission lines (such as printed circuit board microstrip line or stripline transmission lines, also employing suitably spaced ground planes and dielectrics), both lines typically arranged in a meander type pattern, and both lines connected to each other by a load resistance. Each line will typically have its own independent conductive backing layer that is configured to follow the course of the printed circuit line, rather than to form a continuous conductive backing layer covering many different printed circuit lines (normally called a "ground plane"). Here, by analogy to the more conventional continuous conductive backing, which is usually called a "ground plane", the invention's novel conductive backing layers that are precisely contoured to follow the shape of the line traces is termed a "split ground plane".

Note that although the term "ground planes" and "split ground planes" are used throughout this disclosure, in another aspect of the invention, not all of these conductive printed circuit backing layers will in fact be connected to the system's electrical ground. As will be discussed, some of these "ground planes" or "split ground planes" will be "floating.

The system will employ a suitably connected power supply and processor controlled high-speed switch. The output of the system is transferred to an insulated electrical antenna proximate a portion of a human user's body.

BRIEF DESCRIPTION OF THE DRAWINGS

FIG. 3B shows an alternative design for a printed circuit board containing two substantially planar microstrip line conducting strips configured in a meander pattern, and separated by a load. Note that only section of the underlying "split ground plane" is electrically grounded, while the other section is "floating".

DETAILED DESCRIPTION OF THE INVENTION

In some embodiments, as will be discussed, the invention may be a pulsed electromagnetic field (PEMF) therapy system or method. The system comprises a PEMF power source, generally encased in a housing, along with insulated electrical antennas configured to deliver PEMF energy to one or more portions of a human body.

The PEMF power source generally comprises a Blumlein transformer circuit (sometimes called in the alternative, a Blumlein transmission line circuit). This Blumlein transformer or transmission line circuit comprises two Blumlein transmission lines of equal length, connected in series to each other by a load resistance. Here the line that is directly connected to the power supply will be called "line-1", and the line that is not directly connected to the power supply (except by line-1 and the load resistor) will be called "line-2".

Figure 2A:
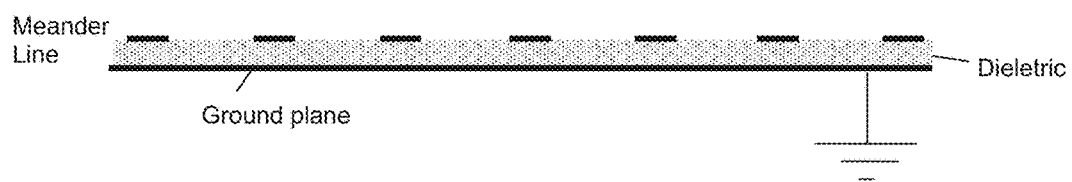
FIG. 2A shows a cross-section of a substantially planar microstrip line type conducting strip, separated from a ground plane by one substantially planar dielectric material. The electrical ground symbol shows that this "ground plane" is grounded.
Figure 2B:
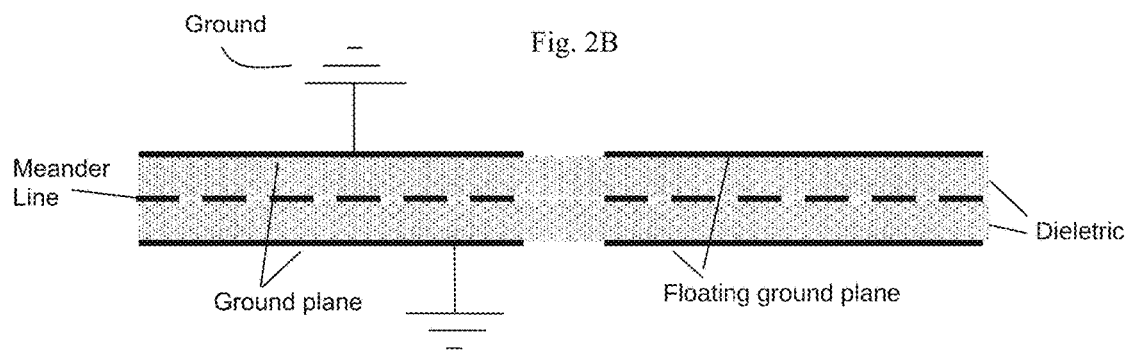
FIG. 2B shows a cross-section of a substantially planar stripline type conducting strip, separated from two ground planes by two substantially planar dielectric materials. Note that the "ground plane" is not always electrically grounded, in which case it is considered to be a floating ground plane.
Figure 2C:
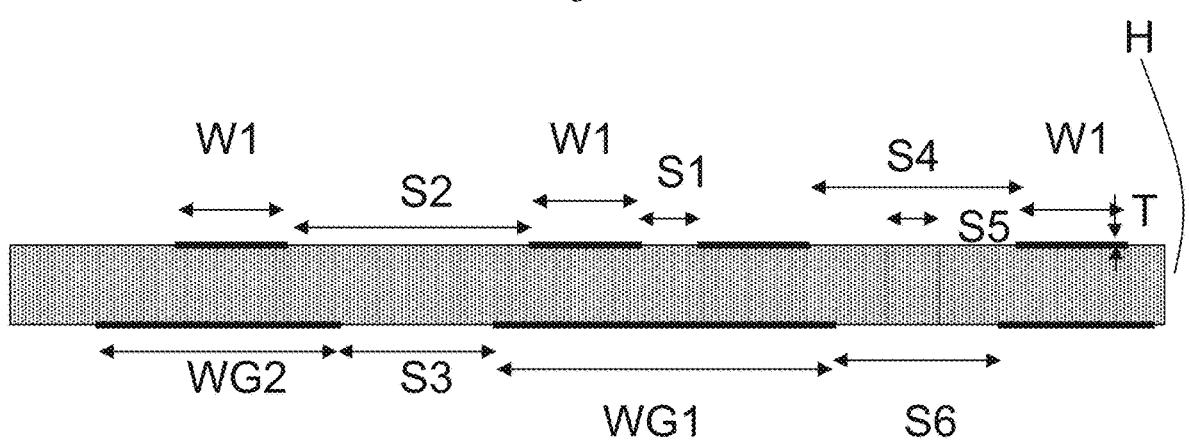
FIG. 2C shows a more detailed cross-section analysis of the various dimensions that may be used in the planar conducting strips used in the Blumlein transformer, previously shown in FIG. 2A and FIG. 2B

According to the invention, the Blumlein transformer/transmission lines here each comprise a substantially planar conducting strip, often mounted on a printed circuit board. This planar conducting strip is preferably configured in a meander pattern, and each strip is separated from at least one ground plane by at least one substantially planar dielectric material, as illustrated in FIG. 2A, FIG. 2B, and FIG. 2C. Thus according to the invention, each substantially planar conducting strip, and each at least one substantially planar dielectric material, and said at least one ground plane form a substantially planar laminated printed circuit board. As will be discussed, since the invention uses two such Blumlein transformer/transmission lines, each based on a planar conducting strip, often it is convenient to mount both conducting strips on the same printed circuit board, as shown in FIGS. 3A, 3B, 4, and 5C.

Figure 7:
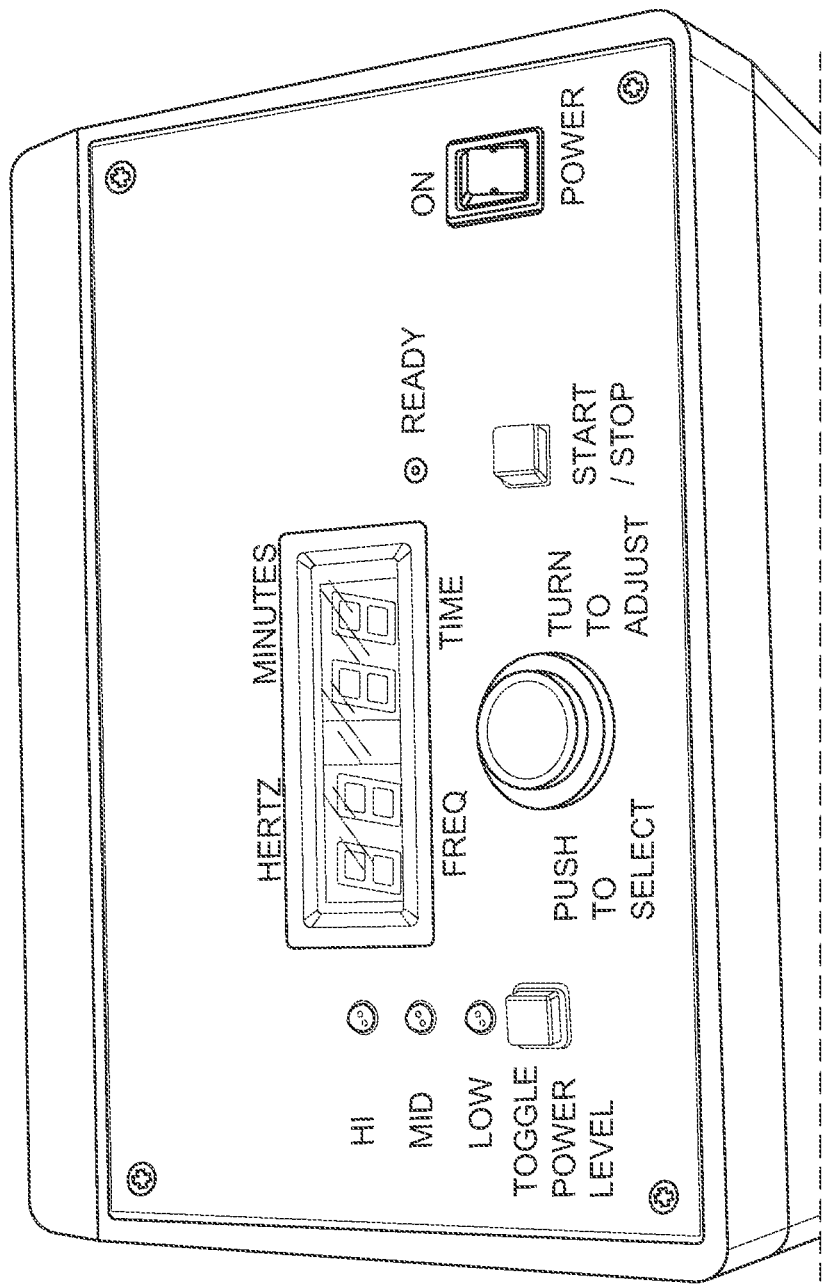
FIG. 7 shows the upper part of the housing previously shown in FIG. 5. This housing further has a control panel comprising a display which can output operating parameters of the device, as well as various controls such as a panel mounted control directing the device's high-speed switch to open briefly between 1-30 times per second, depending on the setting of the control.
Figure 8:
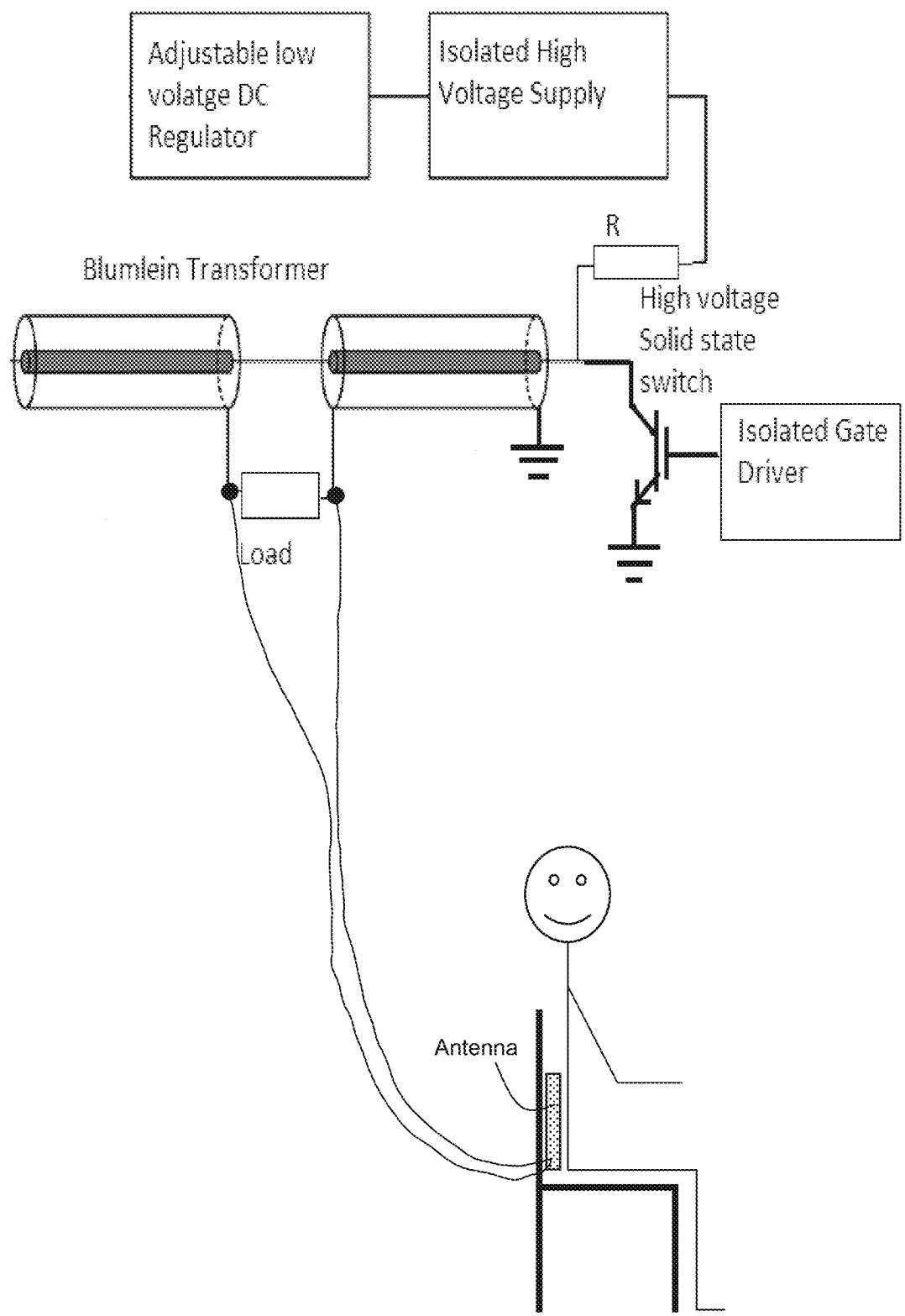
FIG. 8 shows the system configured with an insulated electrical antenna that is configured as part of a seat cushion, along with a user receiving PEMF therapy from the system.

As shown in FIG. 8, this Blumlein transformer circuit is connected to a power supply and a processor-controlled high-speed switch, so that when the switch is open, the Blumlein transformer circuit and transmission lines become charged, electrical energy is stored in the dielectric material. When the switch is closed, this electrical energy rapidly collapses, producing a short duration (e.g. 1-50 nanoseconds) high voltage pulse (e.g. a pulse of high voltage output, see FIG. 6) of the Blumlein transformer circuit across the load resistance. As FIGS. 7 and 8 shows, the high voltage output of this Blumlein transformer circuit connected to an output interface mounted on the housing, so that the high voltage pulse can be transferred (using suitable conducting wires) to an insulated electrical antenna proximate a portion of a human user's body.

Blumlein Transformer/Transmission Line Discussion:

In the invention, the Blumlein transformer circuit operates as a cascaded transmission line of two equal lengths. The output is taken across the non-energized 'ground' connections of each line. Note that only one end of the first transmission line section is actually connected to the system ground. The second transmission line is actually floating away from the electrical ground, so that the propagated pulse is coupled to the ground or return part of the transmission line.

Further, in a Blumlein transformer, the load is connected in series between two equal length transmission lines, which are charged by a DC power supply at one end (note that the right-hand line in FIG. 8 is charged through the impedance of the load).

The present invention can be implemented using various types of planar conducting strip designs. In some embodiments, the at least one ground plane can be one ground plane, the at least one substantially planar dielectric material can be one substantially planar dielectric material. In this embodiment, the substantially planar laminated printed circuit board thus creates "microstrip line" type transmission line(s).

FIG. 2A shows a cross-section of a substantially planar microstrip line type conducting strip, separated from a ground plane by one substantially planar dielectric material.

Alternatively, the at least one ground plane can be two ground planes (mounted facing each other), the at least one substantially planar dielectric material can be two substantially planar dielectric materials, and the substantially planar conducting switch can be positioned in-between the two substantially planar dielectric materials. Further, the two substantially planar dielectric materials can be positioned in-between the two ground planes. In this embodiment, the substantially planar laminated printed circuit board thus creates a "stripline" type transmission line.

FIG. 2B shows a cross-section of a substantially planar stripline type conducting strip, separated from two ground planes by two substantially planar dielectric materials.

Although the planar conducting strip can be arranged in various configurations, in a preferred embodiment, the conducting strip will be arranged in a meander configuration. Even here, there are various design decisions that can be made.

The invention is inspired, in part, by the fact that there are some complexities to consider. When an "ideal" meander type conducting strip line is used to implement a Blumlein transformer on a printed circuit board (PCB), note that at very short time intervals, there is no actual ground plane, but instead there is a ground path that follows the energized strip conductor. That is, in the time frame of the very short duration Blumlein pulse (typically only a few nano-seconds long), the input ground connection is quite different from the point where the load is connected to the same metal trace. This is because when viewed on nanosecond time scales, it takes time for the pulse to propagate down the transmission line. During this propagation time, at two different points on the PCB (input and load points) the, input and load actually experience different electrical conditions over nanosecond time intervals. This occurs even though at longer time durations (e.g. direct current conditions) the two points, because they are directly connected, would otherwise be expected to be experiencing the same electrical conditions (because they are connected by a good conductor). In some embodiments, the invention may take these considerations into account.

In some embodiments, when both of the (meander) transmission lines are mounted on the same substantially planar laminated printed circuit board, a proximal end of a first transmission line that is distal from the load resistance may be connected to the power supply, and the processor controlled high-speed switch. Further, a distal end of a second transmission line that is distal from the load resistance and distal from the power supply and the processor controlled high-speed switch can be configured to be electrically floating.

Given the very short pulse time durations, the dimensions of the meander line configuration can be important. FIG. 2C shows a more detailed analysis of the various dimensions that may be used in the planar conducting strips used in the Blumlein transformer, previously shown in FIG. 2A and FIG. 2B.

In FIG. 2C, the circuit board shows a cross-section of a configuration where there are two sets of meander lines on the printed circuit board, each set implementing a transmission line. Here each transmission line will be designated as a printed circuit board section (e.g. section 1 and section 2). The dimensions for the meander line(s) comprise, two sections of cascaded transmission line, as can be seen in more detail in FIG. 3, FIG. 4, and FIG. 5C.

EXAMPLES

In some embodiments, the configuration of the invention's meander line(s) may be as follows:
- W1=0.040 inch (meander line conductor, typically constant width)
- S1=0.085 inch (typical spacing between consecutive loops of the meander conductor)
- S2=0.13 to 0.18 in (loop spacing with external connection, typically input or load for one section of meander conductor)
- S3=0 0.085 to 0.125 in (similar to S2 except for spacing of the ground paths associated with meander line)
- S4=0.25 inch (spacing between the two sections of Blumlein transformer for the meander conductor)
- S5=0.10 inch (this can be cut into the printed circuit board with an air dielectric to improve (increase) the breakdown voltage between two sections of the Blumlein transformer)
- S6=0.175 inch (similar to S4 except for the ground path spacing between sections of Blumlein transformer)
- WG1=2.2 in (width of bulk of meander ground plane, required to minimize area)
- WG2=0.12 in (needs to be typically wider than W1 and less than 3×W1)
- W/H=0.65 (this is the impedance of the line)
- T=1 oz. copper or 0.0014 inch (standard thickness of PCB copper trace)
- H=0.062 inch (standard thickness for PCB)
- Length of meander line=120 to 150 inches
- Meander line PCB area=~5×5 inch
- Dielectric material=FR4
- Operating voltage 3000 Volts (DC) or higher Higher values for any of these may also be used, such as 2×, 4×, and 8× the above examples. Similarly, lower values for any of the above may also be used, such as ½, ¼, and ⅛ the above examples.

Thus for example, in some embodiments, on the printed circuit board, each transmission line will typically have a length of at least 30 inches, and a width of at least 0.020 inches. Further, the meander pattern will typically compress a total length of each transmission line into a series of at least 4 connected smaller and substantially parallel linear segments.

In this context, the term "split ground plane" can be understood to mean that the "split ground plane" is configured to trace a path underneath the transmission line in a manner so that the split ground plane follows the path of these at least four connected smaller and substantially parallel linear segments.

Although, as voltage of system increases to still higher values than listed in the above example, the same topology can be used as shown in FIG. 2C and elsewhere. However some of the various dimensions and other parameters may need to be hanged. Specifically, at higher voltages:

S1, S2, S3 and H should increase to prevent electrical shorts (arcing)

T and W1 should also be increased to keep the series resistance low as the resultant current increases FR4 is a commonly used printed circuit dielectric, and has the advantage of low cost. However, at higher voltages, the type of dielectric material used may also need to be changed in order to prevent arching.

Depending on nature of switch and number of cascaded switches, used at higher voltages, rise time may increase resulting in longer transmission lines, conversely with more specialized faster switches can result in faster rise time resulting in shorter transmission line length As a result there can be a considerable amount of variation actual dimensions for a specialized Blumlein meander line transformer As another example of a range of values for the previously discussed parameters:

W1 can be between 0.010 to 0.5 inch
S1 can be between 0.02 to 1.0 inch
S2 can be between 0.02 to 1.2 inch
S3 can be between 0.02 to 1 inch
S4 can be between 0.1 to 2 inch
S5 can be between 0.01 to 1 inch
S6 can be between 0.025 to 2 inch
WG1 can be between 0.25 to 5+ inches
WG2 can be between 0.02 to 0.6 inches
W1/H can be between 0.1 to 2
T can be between 0.5 to 5 ounce copper or 0.0007 to 0.007 inch thick
H can be between 0.032 to 0.5 inch
Length of meander line can be between 20 to 300 inches
Dielectric material can be any high voltage breakdown printable dielectric or composite (e.g. a PCB with extra high quality dielectric layer(s) if necessary to prevent breakdown at high voltages)
Operating voltage can be between 500 to 50,000 volts DC.

Figure 3A:
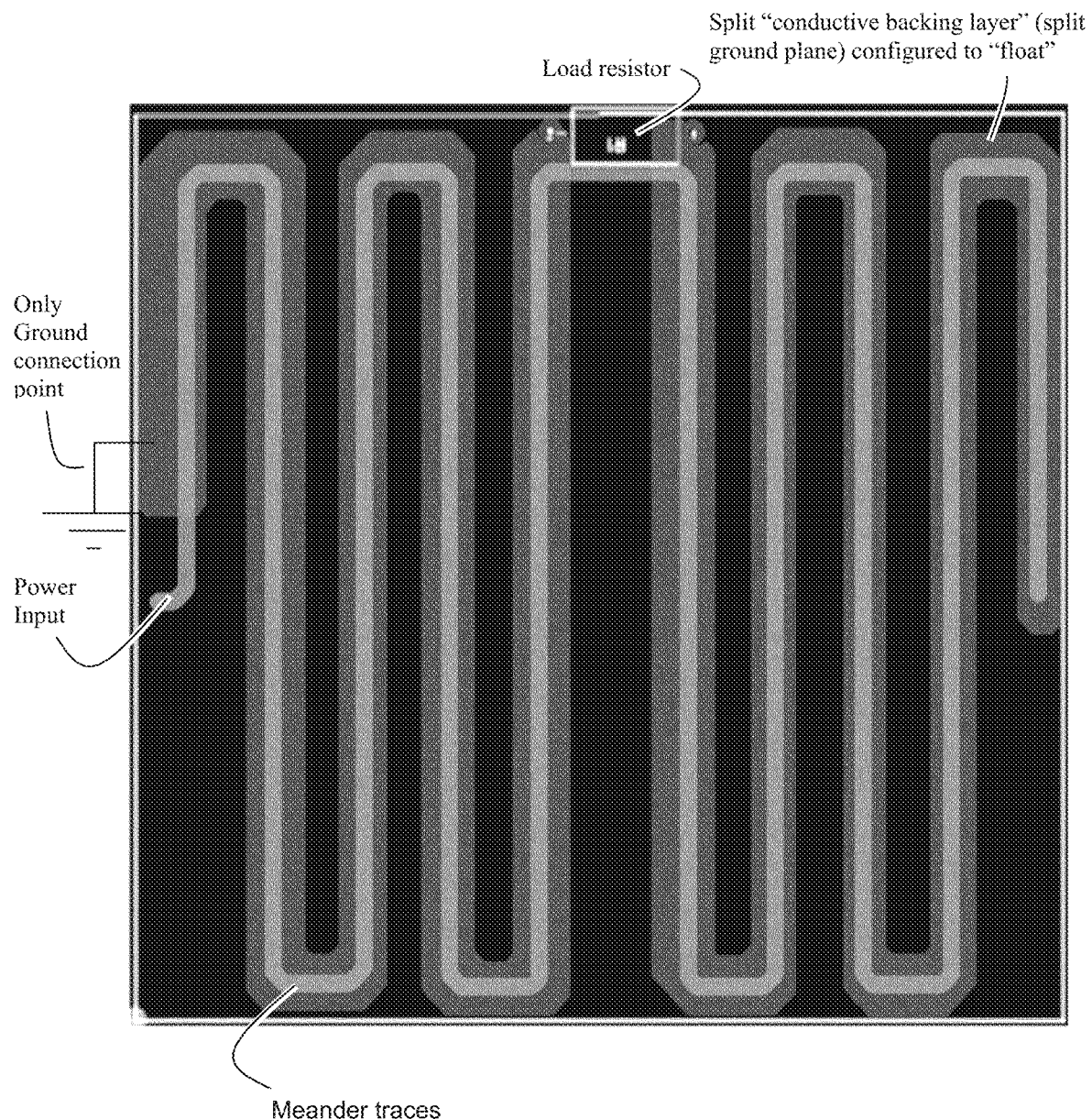
FIG. 3A shows a first design for a printed circuit board containing two substantially planar microstrip line conducting strips configured in a meander pattern, grounded at one end only and separated by a load.

FIG. 3A shows a first design for a printed circuit board containing two substantially planar microstrip line conducting strips configured in a meander pattern, and separated by a load.

According to the invention, the meander line(s) with associated meander ground path(s) approximates the coax type transmission lines more commonly used in Blumlein transformer circuits. However, to achieve good results, extra space is needed to keep the ground path separated to prevent high voltage breakdown which may otherwise effectively short out the meander delay, thus resulting in an inefficient use of printed circuit board area.

The invention is based, in part, on the insight that the pulsed ground current only effectively exists directly under the conducted meander line. This insight allows the resultant printed circuit Blumlein transformer circuit structure to be space minimized, with little negative impact on performance.

The invention is also based, in part, on the insight that for this type of circuit, in order to achieve higher output pulse voltages, the conventional printed circuit board teaching that all conductive backing layers ("ground planes") on a printed circuit board should be connected to an electrical ground should not be followed.

In FIG. 3A, the Blumlein meander line configuration uses "split" ground planes in order to compress the printed circuit board area required to implement the circuit. Here, the word "split" is intended to convey that conductive printed circuit board layer underlying the meander lines is not a continuously connected conductive material backing that underlines many line traces simultaneously, but is instead a conductive material backing that closely follows the shape of the meander line trace, with gaps between traces, thus creating a more topologically complex "split" like configuration, here referred to for simplicity as a 'split ground plane".

Note also that according to the invention, the conductive material backing that closely follows the shape of the "line-1" meander line trace ("line-1 split ground plane") is not electrically connected to the conductive material backing that closely follows the shape of the line-2 meander line trace ("line-2 split ground plane"). Instead, only the line-1 split ground plane is connected to the electrical ground, while the line-2 split ground plane may be electrically floating.

By contrast, in the prior art of Romeo, both of their lines (Romeo FIG. 3) were spiral lines that used only used a single continuous ground plane as a reference, normally at a ground or zero volt potential.

However the invention is also based on the insight that according to the present invention, the energy/charge is obtained largely from the ground instantaneous potential. As a result, other factors need be considered.

Here, note that in the embodiment of the invention, shown in FIG. 3A, the load R1 is connected between the two ground paths. This more compact structure, still maintains the effective length or signal delay of the ground structure, by a partial split at the input and output of each meander line. This partial split in each of the ground 'planes' is used to approximate a 'coax' type line with a distributed ground as opposed to a lumped ground for the meander configuration. Normally there is little distinction between the two structures, coax and meander line, for a signal delay function however in this case the differences are critical as this is one of the few cases where the output is taken from the 'ground' side only.

Thus in the configuration shown in FIG. 3A, in FIG. 3A there is a "split ground plane" comprising a conductive underlying "ground" structure that closely follows the path of the meander line circuit trace.

For example, as shown in FIG. 2C, if the circuit trace has a width of W1, the underling conductive path (e.g. split ground plane) WG2 will typically have a width greater than W1, but less than 3 times the width of W1. So if W1 is 0.04 inches wide, WG1 may have a width between 0.04 inches and 0.12 inches.

By contrast, in non-spit situations, the underlying conductive path WG1, (standard or non-split ground plane), which will cover more than one circuit trace W1, will often have a width of 1.0 inches or more.

By contrast, FIG. 3B shows a continuous and more topologically compact "lumped" ground plane structure that does not follow the path of the meander line circuit trace.

The "ground plane" in FIG. 3B instead underlies many such traces without regard to the actual shape of the meander line trace above. This is considered to be a standard or "non-split" ground plane.

FIG. 4A shows another example of the invention's meander line concepts, here implemented over a "lumped" or standard ground plane design, similar to that previously shown in FIG. 3B.

Figure 1:
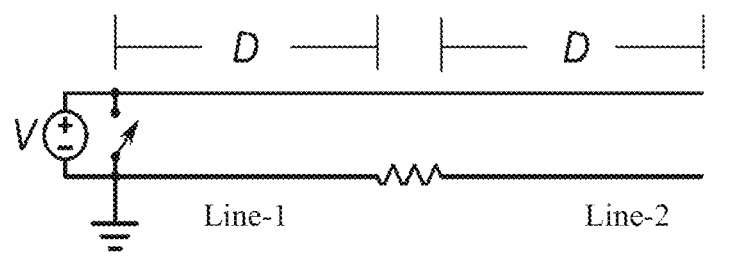
FIG. 1 shows a schematic diagram of a prior art Blumlein transformer circuit. Note that for future reference, the line directly connected to the power supply is designated "line-1", and the line only connected to the power supply by a load resistor is designated "line-2".
Figure 1:
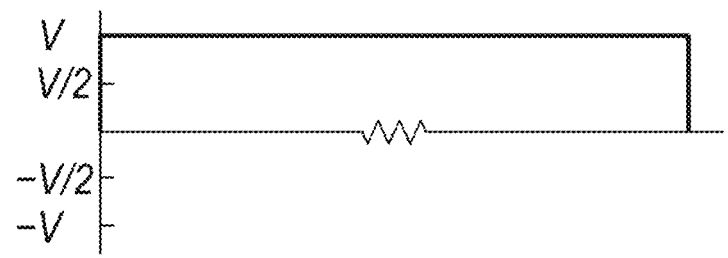

The invention is based, in part, on the insight that without these splits in the ground path (for example on input side near the load) the output voltage would be reduced by a factor of two, because the ground path cannot swing negative, see FIG. 1, and would instead is thus be forced to operate at ground potential. This has the disadvantage that the differential voltage across the load is halved, e.g. half of the value that can be obtained using the embodiment shown in FIG. 4.

A key insight behind the present invention is that the propagating edge, that defines the pulse, induces a like charge instantaneously directly under the meander line to the ground structure. For the standard ground plane configuration shown in FIG. 3B, normally this would not be a problem. However when one needs to extract the charge from the ground side of the circuit, then the circuit structure needs to behave like more like a coaxial cable. The split ground plane configuration shown in FIG. 3A, where the ground plane follows the shape of the meander line traces, provides the printed circuit version of a coaxial cable structure that provides a compact "coaxial cable on a printed circuit board" configuration that provides both high voltage and fast nano-second pulsed output.

The meander line trace can thus be separated, by at least one dielectric layer, from at least one underlying conductive layer (e.g. ground plane). This underlying conductive layer can have more than one configuration. In some regions, the underlying conductive layer can be a "split" conductive layer that precisely follows the path of the meandering conductive layer above it. This can be designated as having a "distributed ground path", at least in the case where this ground path is grounded. In other regions the underlying conductive layer can be a more traditional non-split or "lumped" conductive layer that can extend over multiple traces. The meander line itself may have some portions of the meander line that pass over this "split" ground plane and other portions of the meander line that pass over a more traditional non-split or lumped ground plane. So some percentage of the meander line may be over a "split" or distributed ground path, while another percentage of the meander line may be over a more traditional "lumped" ground path or ground plane.

Note that according to the invention, the percent of the meander line that is over a distributed ground path (i.e. has its own ground plane that precisely follows the contour of the meander line), versus the percentage of the meander line that is over a lumped (i.e. no separation between traces) ground plane, defines the degree of approximation that the meander line approximates that of an ideal coaxial Blumlein transformer. In general, to achieve the full supply rail nano-second pulse amplitude while maintaining a compact form of a full meander line structure, an appreciable extent of the meander line, such as 50% of the meander line or greater, will be over a distributed or "split" ground path.

In some embodiments, to implement a compact Blumlein transformer design, while at the same time achieving a Blumlein output pulse of the desired magnitude, the meander line may be implemented in a hybrid fashion where part (usually 50% or greater) of the meander line is over a "split" ground plane, while the remaining part of the meander line may be over a more conventional "lumped" ground plane that extends over multiple traces.

Microstrip Vs Stripline Considerations

As previously discussed, the meander line can be implemented in either a microstrip two-layer PCB configuration (FIG. 2A) or as a stripline four-or-greater layer PCB configuration (FIG. 2B). There are various trade-offs between these different designs.

The microstrip (two-layer) approach generally can be implemented on a lower cost PCB. The resulting PCB layout can be more efficient, because the two-layer design does not require extra areas to stitch the top and bottom layers together with printed circuit vias. However, the microstrip approach has the disadvantage that relative to the stripline four-or-greater layer configuration, the microstrip two-layer configuration for the same width conductors, has about half the capacitance. This limits the output current of the microstrip configuration.

For the stripline (four-or-greater layer) approach, the stored electrical energy is essentially entirely contained in the PCB structure, and this configuration produces about twice the coupled capacitance and resulting higher output current. However the stripline approach does take more PCB area to stitch the top and bottom layers together, and such four-or-greater layer stripline PCB tend to cost significantly more than the two-layer microstrip PCB design.

Note further that the impedance of the Blumlein transmission line, and thus the current carrying capacity and the packing density of the structure, is determined by the width of the PCB conducting strip traces, relative the thickness of PCB dielectric. Wider strip traces result in a larger amount of effective capacitance available to discharge into the load, but this will also take longer to dis-charge up as well, resulting in slower rise times. Other factors influence rise times as well, including the gate capacitance of the device's solid state switch (typically an FET or IGBT type), the number of cascaded switches (if any), parasitic inductance around the switch, the gate driver rise times and current capability, and so on.

High Voltage Considerations

FR4 is a commonly used printed circuit dielectric material. Under normal conditions, standard FR4 material of standard thickness (e.g. $\frac{1}{16}$ inch thick material) can handle several thousand volts without suffering corona or dielectric breakdown (leading to PCB failure). However, for more powerful (higher voltage) implementations, other materials may need to be considered. Note that in this context, although the published dielectric strength of FR4 is about 800 v/mil thickness, moisture can significantly lower this. Thus the user of other printed circuit board dielectrics with higher ratings may be advantageous. Here the relative ratings of some alternative dielectric materials include:

FR4 800 v/mil
BT epoxy 1300 v/mil
polyimide 900 v/mil
HVPF 3000+v/mil

Thus in some embodiments, additionally, use of barrier dielectric materials with ratings higher than FR4 may be used.

Returning to FIG. 4, this figure also shows a preferred design for a printed circuit board containing two substantially planar microstrip line conducting strips configured in a meander pattern, and separated by a load. This improved design further comprises isolated ground paths and floating ground planes.

As previously discussed, this planar transmission line is a modified meander line with split ground planes. Here the floating ground plane, that is the actual output, is sliced or split to approximate a coaxial transmission line, which also helps reduce the pulse's rise time. Note that as previously discussed, at higher voltages, some care needs to be taken to ensure corona breakdown of PCB does not.

Powering the Blumlein Transformer Circuit

The Blumlein transformer circuit requires an input power supply and other control circuitry. An example of such a power supply is shown in FIG. 5A, and an additional example is shown in FIG. 5B.

Typically, this power supply will further comprise an adjustable low voltage DC regulator configured to drive a high voltage supply configured to provide input electrical power to the Blumlein transformer circuit. A resonant transformer may be used to step up the input voltage (such as 12-volt input voltage) to higher voltages required to drive the Blumlein circuit. Although such resonant transformers provide low current levels (typically around 10 milliamps), they are otherwise a very cost-effective way to get high voltage from a small package size. Such resonant transformers often occupy about 1-2 cubic inches in space, which is useful when small and portable PEMF devices are desired.

Figure 5A:
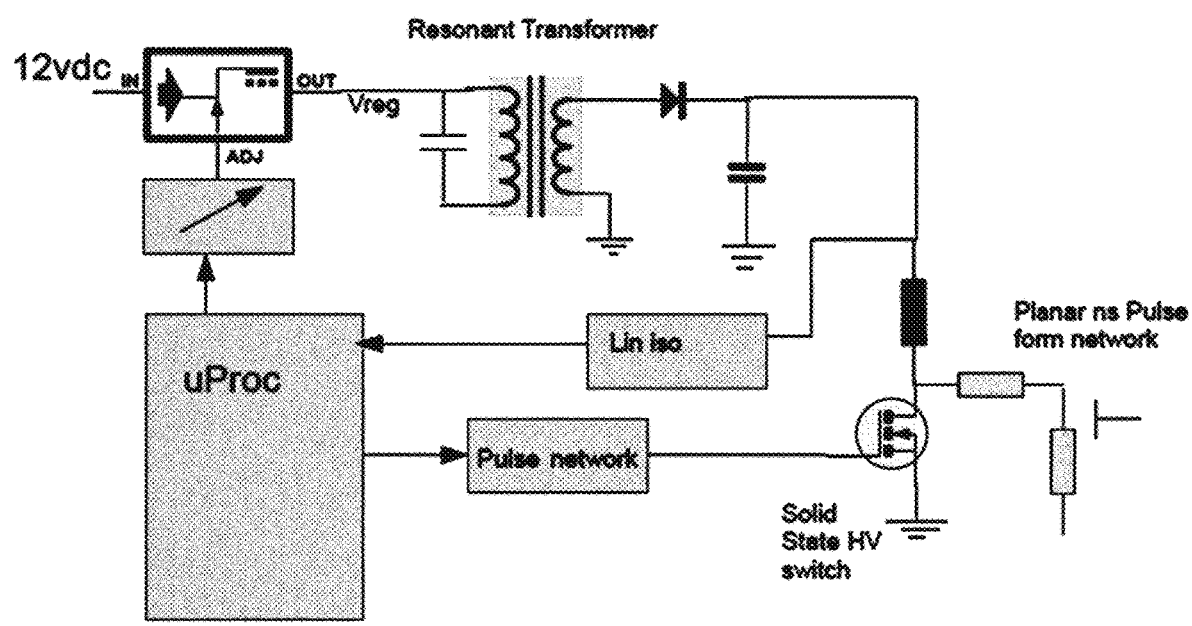
FIG. 5A shows one embodiment of the device's power circuitry.

Thus in some embodiments, as shown in FIG. 5A, the system may use an adjustable low voltage DC regulator such as a 12 volt DC regulator, and the high voltage supply can further comprise a resonant transformer configured to produce an output voltage of at least 1 kilovolt.

Figure 5B:
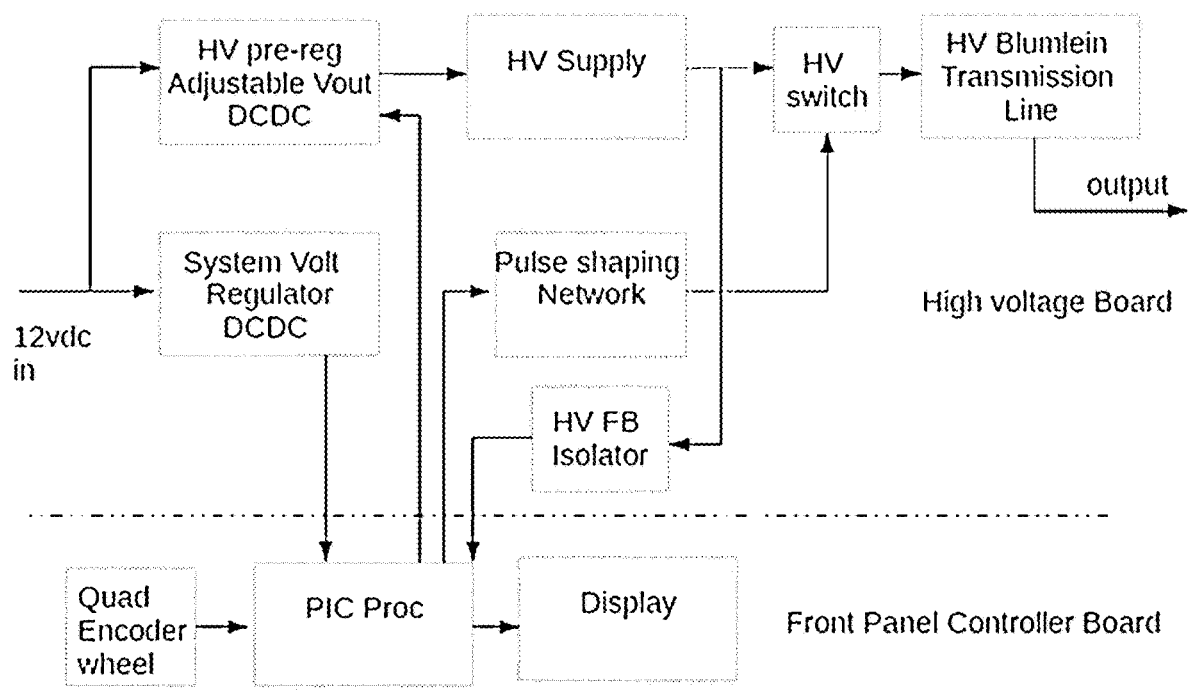
FIG. 5B shows additional detail of the device's power circuitry.

FIG. 5B shows additional detail of the device's power circuitry, including details of how the power circuitry may interface with the various input devices and displays on the control panel shown in FIG. 7.

Figure 4:
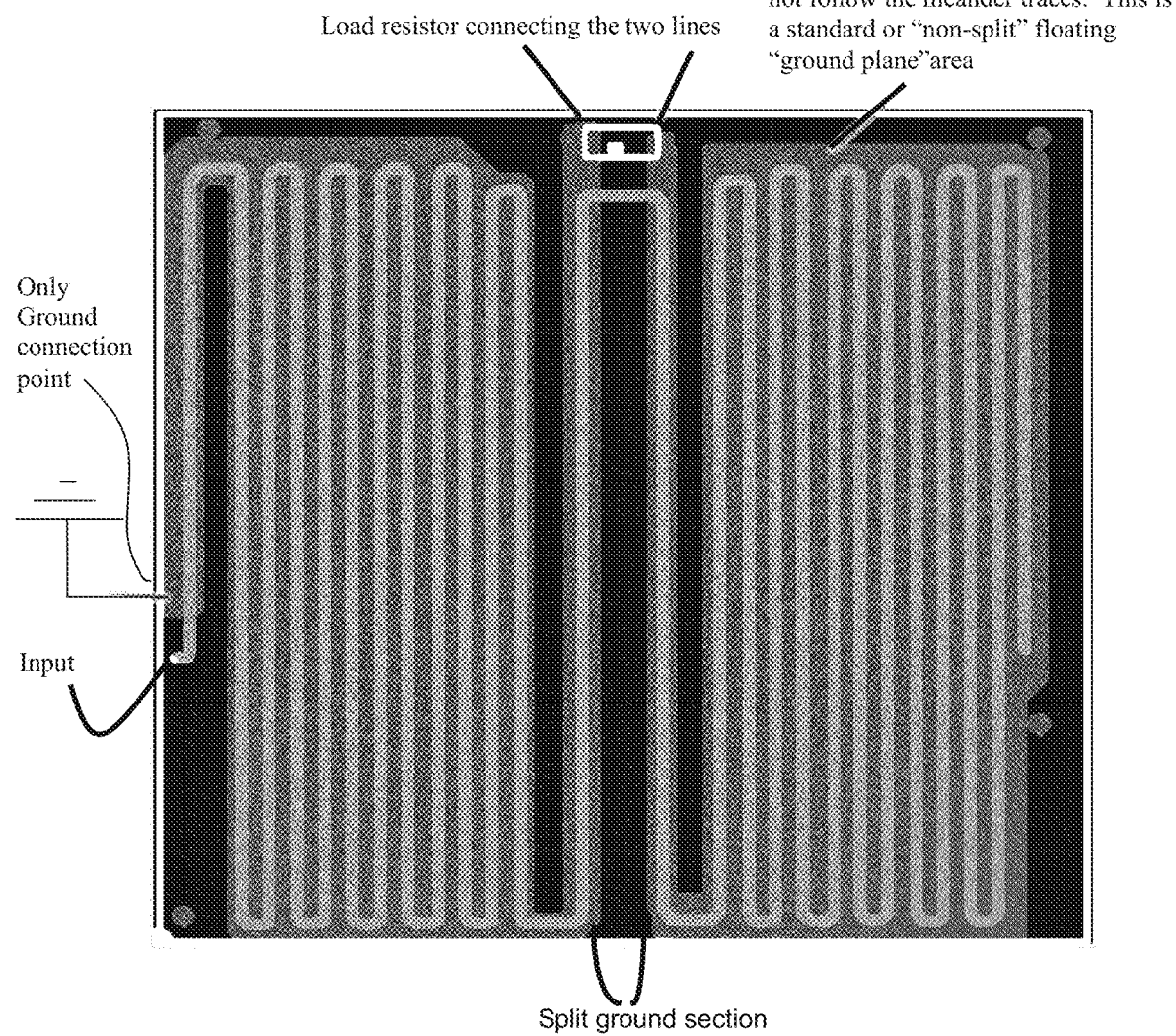
FIG. 4 shows a Blumlein meander line that uses "lumped" ground planes in order to reduce the printed circuit board area required to implement the circuit, while also providing higher output pulsed voltages. This printed circuit board contains two substantially planar microstrip line conducting strips configured in a meander pattern, and separated by a load. This improved design further comprises isolated ground paths and floating ground planes.
Figure 5C:
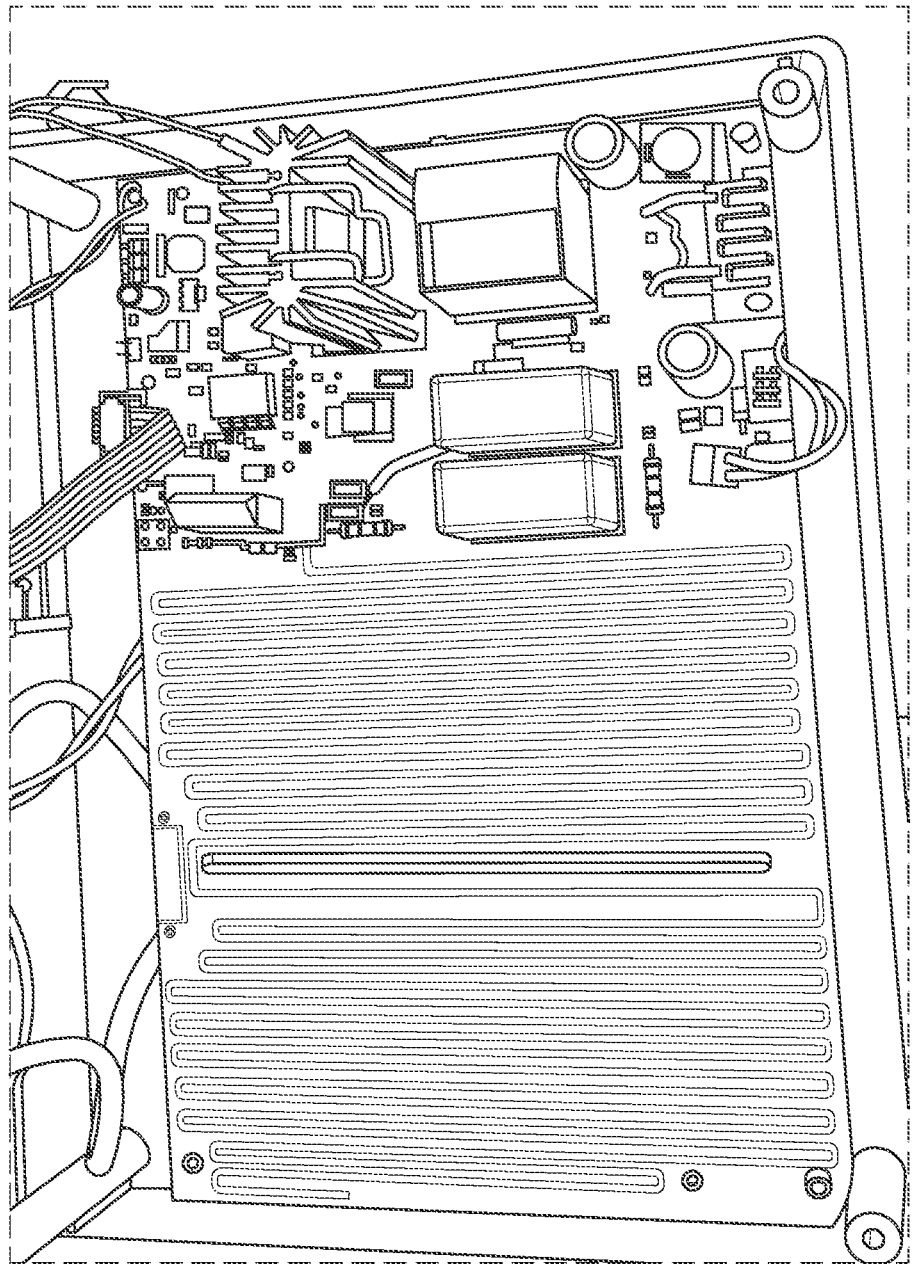
FIG. 5C shows the preferred printed circuit board from FIG. 4 configured in the lower part of a housing, and connected to a power supply and processor controlled high-speed switch.

FIG. 5C shows the preferred printed circuit board from FIG. 4 configured in the lower part of a housing, and connected to a power supply and processor controlled high-speed switch.

Here the high voltage solid state switch shown in FIG. 5A may be an insulated-gate bipolar transistor (IGBT) device, or a high voltage field effect transistor (FET) device. One example of such a switch is an IXBH20n360HV BIMOS-FET device, produced by IXYS Discrete Semiconductor Products, which is rated at 3600 volts and 200 A for 1 millisecond. The resonant transformer shown in FIG. 5A may be a high voltage high-frequency miniature ferrite transformer, such as a 28k089 7 kv 10 ma high voltage transformer, available from Amazingone.com.

Timing Considerations:

There are two different types of timings involved in the invention, one is the timing in which the Blumlein transformer circuit is energized from the power supply, and the other is the timing of the very short duration Blumlein output pulse.

With regards to the circuit that energizes the Blumlein transformer circuit, this is the circuit shown in FIG. 5A that triggers the high voltage insulated-gate bipolar transistor (IGBT) device. Here the system microprocessor ("uProc" in FIG. 5A) is typically configured (often by a control panel input) to generate between about 1 to 30 square waves per second. The circuit can optionally also employ a delay integrated circuit chip that delays this square wave signal by 0.1 to 0.5 microseconds by, for example using different 5 IC tap point leads on the delay chip.

Thus in some embodiments, the original square is subtracted from the delayed square wave, resulting in about a 0.2 microsecond pulse every 1 to 1/30 seconds (e.g. 1-30 Hz), depending on the frequency selected by the user (again often using the front panel control, labeled "ADJ" in FIG. 5A).

This short pulse is in turn fed to an isolated gate driver IC ("Lin iso" in FIG. 5A), which galvanically isolates the signal, and provides a high current driving signal to turn 'on' the IGBT quickly as possible.

Timing Considerations of the Blumlein Transformer Generated Output Pulse

When the solid state HV switch (IGBT) is turned "off", the high voltage generated by the high voltage resonant transformer (after being rectified with the half-wave rectifier circuit and the high voltage diode and capacitor bank shown in FIG. 5A), charges up the Blumlein transmission line (see FIG. 8).

When the solid state HV switch (IBGT) switch is turned "on" by the isolated gate driver (see FIG. 8), the voltage to the Blumlein transformer rapidly decreases to approximately zero volts over a few nanoseconds such as about 20 nanoseconds. Remember that there is energy stored in printed circuit board meander line dielectric. When the solid state HV switch is turned "on", this stored energy field collapses, causing a negative transition voltage that propagates down the Blumlein transmission line until it hits the load resistor, see FIG. 1. When this happens, part of the signal is reflected and other part continues on. This ultimately generates the very brief (tens of nanoseconds duration) Blumlein output pulse shown in FIG. 6, which ultimately is used (with the antenna device discussed shortly) to deliver PEMF energy to the patient.

An important consideration regarding the length of the transmission line(s) of the Blumlein transformer are that they need to be long enough to provide time, during the rapid collapse of the stored energy field, for the brief transition pulse to fully occur before cancellation occurs due to the reflected pulse from the opposite Blumlein transmission line.

Figure 6:
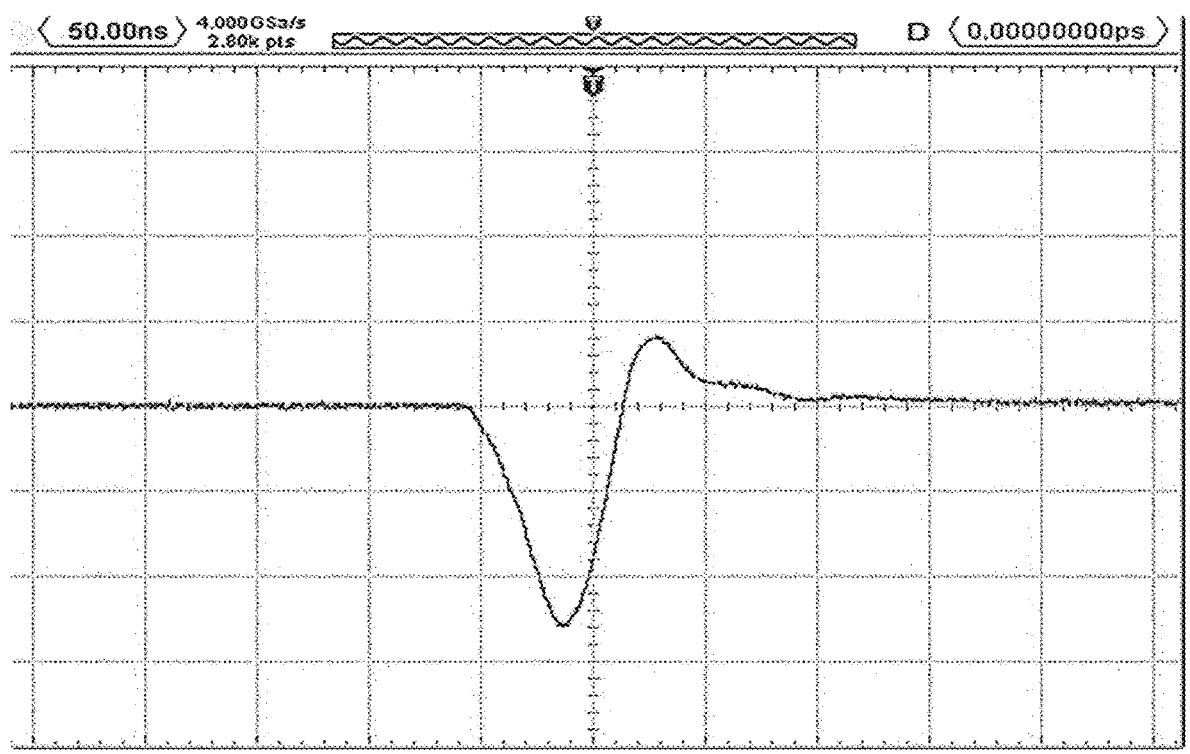
FIG. 6 shows an example of the high voltage pulse emitted by the device shown in FIG. 5.

Given that each section of the Blumlein transformer is of equal length, and that the lengths should be long enough for the transition time of the switch, then the characteristics of the brief high voltage pulse shown in FIG. 6 is determined by the geometry of the two Blumlein transmission lines.

From a Fourier analysis perspective, the radio frequency (RF) aspects of the high voltage Blumlein pulse shown in FIG. 6, where the pulse has a rise time of about 20 nanoseconds, means that in the frequency domain, and assuming the rule of thumb formula:

$$\text{Bandwidth [GHz]} = \frac{0.35}{RiseTime[\text{nanoseconds}]}$$

Thus the RF bandwidth of the Blumlein pulse shown in FIG. 6 is roughly 20 MHz

As shown in FIG. 5A, FIG. 5B, and FIG. 7, in some embodiments the system's processor is configured to receive input from at least one of a panel mounted control directing the high-speed switch to briefly open at least once per second, and no greater than approximately 30 times per second. In alternative embodiments, other input devices, such as remote mounted controls or external wireless devices may also be used. In these alternative embodiments, the system microprocessor may further comprise an interface, such as a wireless network interface (e.g. Wi-Fi, Bluetooth) to enable such alternative inputs.

Note that the physical length of the meander is material specific. When the emphasis is on optimizing the time delay, the key consideration is that each section of the meander line should be configured to be a minimum of ½ the rise time. So delay time is often the primary design consideration, and may often be regarded as being the critical parameter here.

As shown in FIG. 5B and FIG. 7, in some embodiments the system housing may further comprise a display, and the processor may be further configured to report the operating parameters of the system's processor.

FIG. 7 shows the upper part of the housing previously shown in FIG. 5. This housing further has a control panel comprising a display which can output operating parameters of the device, as well as various controls such as a panel mounted control directing the device's high-speed switch to open briefly between 1-30 times per second, depending on the setting of the control.

Antenna Output

In order to usefully apply PEMF energy to a patient, the energy from the high voltage Blumlein output pulses need to be directed to the desired portions of a patient's body using a suitable antenna system.

In some embodiments, the PEMF antenna can be formed from a single spiral coil antenna. As shown in FIG. 8, this antenna is connected to the main unit's Blumlein transformer via high voltage pair of wires. These high voltage wires are typically mounted in a protective tubing to provide additional safety protection for the user from the high voltage discharge (the Blumlein pulse).

In some embodiments, the single spiral coil can be a 6 to 8-inch diameter electrically conducting coil antenna, mounted inside a 12×12 inch structure, and covered with a dielectric cover. This spiral coil can be formed, for example, by three to six turns of an electrical conductor such as an electrical wire. Here the number of turns can vary depending on the type of coil insulation, and the thickness of the coil's electrical conducting material. In a preferred embodiment, the coil can be made from an electrical conductor such as copper, preferably #14 gauge copper wire or thicker. The antenna dimensions can be ¼, ½, 1×, 2×, and 4× the above values, however.

In general, low resistance electrical conductors such as copper are preferred, and the higher the operating voltage of the device, the higher the current that the coil antenna needs to handle. Thus there is a requirement for more copper in the coil antenna with increased operating voltage increases. For example, at higher Blumlein pulse voltages, 0.125 or 0.25-inch outer diameter copper tubing, with an insulated sleeve may be used for the antenna coil.

Thus in some embodiments, the electrical antenna comprises at least 2 feet of an electrical conductor folded into a substantially flat circular or rectangular structure with an approximate surface area between about 10 and 2000 square inches.

The antenna is typically covered by an insulator, such as a dielectric cover that can extend on the top, bottom, and all sides of the antenna coil. This dielectric antenna covering can made from 1/16 inch thick polycarbonate sheet or other material. This thickness of polycarbonate sheet provides good dielectric strength and physical flexibility, yet tends to avoid cracking. Foam padding can also be is added for additional comfort.

Figure 9:
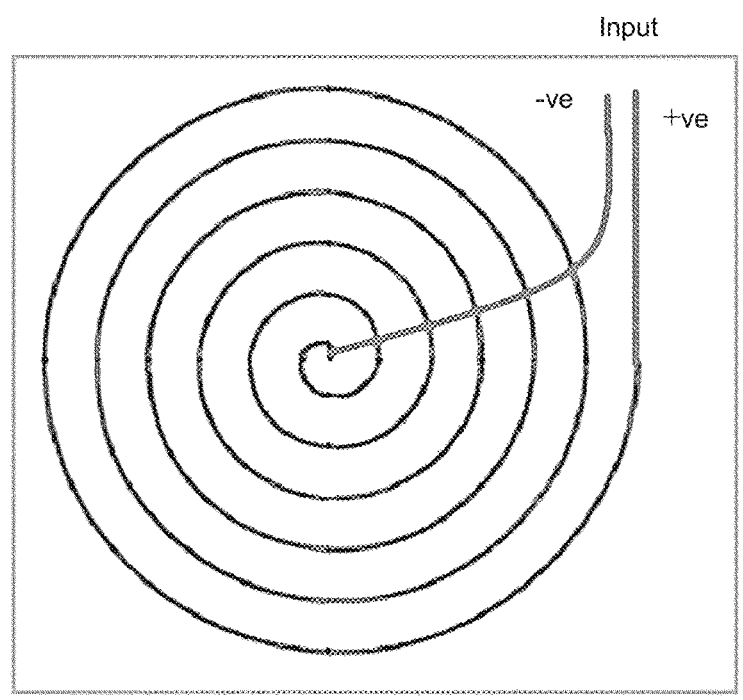
FIG. 9 shows an example of the insulated electrical coil type antenna that is configured to be placed within two inches of a portion of a human body.
Figure 10:
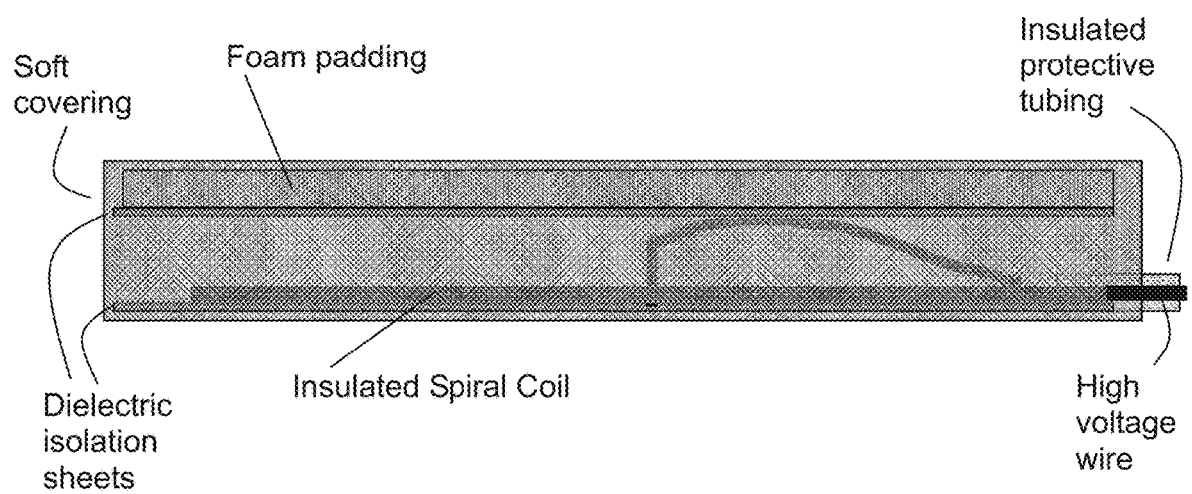
FIG. 10 shows a cross-section of the insulated electrical coil type antenna shown in FIG. 9, illustrating more aspects of the insulation and padding.

As shown in FIGS. 9 and 10, the center electrical connection to the coil antenna can typically be made on the low potential side of the power supply, and it can be implemented as a "fly-over" electrical connection to the high voltage wire from the Blumlein transformer output.

In other embodiments, additional coil type antennas can also be used to provide more effective coverage for the user, and/or to cover both sides of the user's body, arm, or leg. In some embodiments, the antennas may be made flexible, and be configured to wrap around a limb or otherwise conform closely to a particular portion of the user's body.

FIG. 8, for example, shows the system configured with an insulated electrical antenna that is configured as part of a seat cushion, along with a user receiving PEMF therapy from the system.

Thus in some embodiments, the system will further comprise an insulated electrical antenna configured to be placed within 2 inches of a portion of a human body, this electrical antenna connected to the device's Blumlein output interface by an insulated electrical conductor. This insulated electrical antenna can be configured to be any of a built-in furniture cushion or a user movable cushion. In use, a user may be instructed to position themselves (or the pad) relative to the pad's insulated high voltage antenna coil so that the antenna coil is placed near a particular area of discomfort on the user's body (the user's lower back, for example), and then turn the unit on and relax for period of time. Typically, the device is configured (often by user-chosen parameters entered via the control panel) to then will turn off automatically once a preset time duration time (e.g. 5 or 10 minutes) has elapsed.

FIG. 9 shows an example of an insulated electrical coil type antenna that is configured to be placed within two inches of a portion of a human body.

FIG. 10 shows a cross-section of the insulated electrical coil type antenna previously shown in FIG. 9, illustrating more aspects of the insulation and padding.

Further Discussion:

In a preferred embodiment of the invention, two ground areas, one each for the two cascaded meander lines, are joining together at the center of the two meander lines by a load resistor.

Across this load resistor the output voltage is differential. That is, the floating (second stage line) side the voltage goes positive (to ½ of the supply voltage) and the other side of the load resistor (the input meander line side) the voltage ideally goes negative (to ½ of the supply voltage). Thus voltage across the resistor, and thus the voltage to the antenna, are differential and at the full supply rail level.

If the ground plane on the first stage was not split (at least near the resistor load) then the whole ground plane would be at zero volts and then the voltage across the resistor would only be ½ the supply rail as this side of the resistor could not go negative. In some embodiments, it may also be useful to provide a similar configuration for the output section as well.

This split in each of the ground "planes" is used to approximate a "coaxial cable" type line with a distributed ground, as opposed to a lumped or continuous ground for the meander configuration. Normally there is little distinction between the two structures, however for the present invention, the differences are critical as this is one of the few cases where the output is taken from the 'ground' side only.

In some embodiments, the meander line would also have a meander ground path, however this can significantly increase the area taken by the printed circuit board.

According to the invention, an important concept is that when the Blumlein field collapses, the propagating edge, which defines the Blumlein pulse, instantaneously induces a like charge directly under the meander line to the ground structure. For most circuit applications, this would not be a problem. However in a printed circuit type Blumlein device, the device needs to extract the charge from the ground side of the circuit. As a result, the printed circuit Blumlein device needs to behave more like a coaxial cable. The present invention provides such as Blumlein coaxial cable structure on a relatively simple and compact printed circuit board, thus providing a compact form that enables the Blumlein fast (nano-second times) high voltage pulse formation.

The invention claimed is:

1. A pulsed electromagnetic field (PEMF) therapy system for a human user comprising:
   a housing enclosing a PEMF power source:
   said PEMF power source comprising a Blumlein transformer circuit connected in series between two equal length transmission lines connected to each other by a load resistance;
   more than 50% of each said transmission lines comprising a substantially planar conducting strip configured in a meander pattern, and separated from at least one split ground plane by at least one substantially planar dielectric material, such that said substantially planar conducting strip, at least one substantially planar dielectric material, and said at least one split ground plane form a substantially planar laminated printed circuit board;
   said Blumlein transformer circuit connected to a power supply and a processor controlled high speed switch, so that when said switch is open, said Blumlein transformer circuit and transmission lines become charged, electrical energy is stored in said dielectric material, and when said switch is closed, said electrical energy rapidly collapses, producing a short duration high voltage pulse a high voltage output of said Blumlein transformer circuit across said load resistance with output greater than 1 kilovolts;
   said high voltage output of said Blumlein transformer circuit connected to an output interface mounted on said housing, so that said high voltage pulse can be transferred to an insulated electrical antenna proximate a portion of a human user's body.

2. The system of claim 1, wherein said at least one split ground plane is one split ground plane, said least one substantially planar dielectric material is one substantially planar dielectric material, and said a substantially planar laminated printed circuit board creates a microstrip line type transmission line.

3. The system of claim 1, wherein said at least one split ground plane is two split ground planes, said least one substantially planar dielectric material is two substantially planar dielectric materials, said substantially planar conducting switch is positioned in-between said two substantially planar dielectric materials, and said two substantially planar dielectric materials are in turn positioned in-between said two split ground planes, and said substantially planar laminated printed circuit board creates a stripline type transmission line.

4. The system of claim 1, wherein both said transmission lines are mounted on the same substantially planar laminated printed circuit board, a proximal end of a first transmission line distal from said load resistance is connected to said power supply and said processor controlled high speed switch, and a distal end of a second transmission line distal from said load resistance and distal from said power supply and said processor controlled high speed switch is electrically floating.

5. The system of claim 1, wherein each said transmission line has a length of at least 30 inches, a width of at least 0.020 inches; and
   wherein said meander pattern compresses a total length of each transmission line into a series of at least 4 connected smaller and substantially parallel linear segments, and wherein each said at least one split ground plane is configured to trace a path underneath said transmission line in a manner so that each said at least one split ground plane follows the path of said at least four connected smaller and substantially parallel linear segments.

6. The system of claim 1, wherein said processor is configured to receive input from at least one of a panel mounted control, remote mounted control, or external wireless device directing said high speed switch to briefly open at least once per second, and no greater than 30 times per second.

7. The system of claim 1, wherein said housing further comprises a display, and said processor is further configured to report operating parameters of said processor.

8. The system of claim 1, wherein said power supply further comprises an adjustable low voltage DC regulator configured to drive a high voltage supply configured to provide input electrical power to said Blumlein transformer circuit.

9. The system of claim 8, wherein said adjustable low voltage DC regulator is a 12 volt DC regulator, and said high voltage supply comprises a resonant transformer configured to an output voltage of at least 1 kilovolt.

10. The system of claim 1, further comprising an insulated electrical antenna configured to be placed within 2 inches of a portion of a human body, said electrical antenna connected to said output interface by an insulated electrical conductor.

11. The system of claim 10, wherein said insulated electrical antenna is configured to be any of a built-in furniture cushion or a user movable cushion.

12. The system of claim 10, wherein said electrical antenna is folds at least 2 feet of an electrical conductor into a substantially flat circular or rectangular structure with an approximate surface area between 10 and 2,000 square inches.

13. A method of applying a pulsed electromagnetic field (PEMF) to a human user's body, said method comprising:
    obtaining a housing enclosing a PEMF power source:
    said PEMF power source comprising a Blumlein transformer circuit connected in series between two equal length transmission lines connected to each other by a load resistance;
    more than 50% of each said transmission lines comprising a substantially planar conducting strip configured in a meander pattern, and separated from at least one split ground plane by at least one substantially planar dielectric material, such that said substantially planar conducting strip, at least one substantially planar dielectric material, and said at least one split ground plane form a substantially planar laminated printed circuit board;
    said Blumlein transformer circuit connected to a power supply and a processor controlled high speed switch, so that when said switch is open, said Blumlein transformer circuit and transmission lines become charged, electrical energy is stored in said dielectric material, and when said switch is closed, said electrical energy rapidly collapses, producing a short duration high voltage pulse a high voltage output of said Blumlein transformer circuit across said load resistance with output greater than 1 kilovolts;
    said high voltage output of said Blumlein transformer circuit connected to an output interface mounted on said housing, so that said high voltage pulse can be transferred to an insulated electrical antenna proximate a portion of said human user's body;
    applying said insulated electrical antenna to said portion of said human user's body; and using said processor to direct said high speed switch to briefly open at least once per second, and no greater than 30 times per second, thereby applying said PEMF to said human user.

14. The method of claim 13, wherein said at least one split ground plane is one split ground plane, said least one substantially planar dielectric material is one substantially planar dielectric material, and said a substantially planar laminated printed circuit board creates a microstrip line type transmission line; or wherein said at least one split ground plane is two split ground planes, said least one substantially planar dielectric material is two substantially planar dielectric materials, said substantially planar conducting switch is positioned in-between said two substantially planar dielectric materials, and said two substantially planar dielectric materials are in turn positioned in-between said two split ground planes, and said substantially planar laminated printed circuit board creates a stripline type transmission line.

15. The method of claim 13, wherein both said transmission lines are mounted on the same substantially planar laminated printed circuit board, a proximal end of a first transmission line distal from said load resistance is connected to said power supply and said processor controlled high speed switch, and a distal end of a second transmission line distal from said load resistance and distal from said power supply and said processor controlled high speed switch is electrically floating.

16. The method of claim 13, wherein each said transmission line has a length of at least 30 inches, a width of at least 0.020 inches; and wherein said meander pattern compresses a total length of each transmission line into a series of at least 4 connected smaller and substantially parallel linear segments and wherein each said at least one split ground plane is configured to trace a path underneath said transmission line in a manner so that each said at least one split ground plane follows the path of said at least four connected smaller and substantially parallel linear segments.

17. The method of claim 13, wherein said processor is configured to receive input from at least one of a panel mounted control, remote mounted control, or external wireless device directing said high speed switch to briefly open at least once per second, and no greater than 30 times per second.

18. The method of claim 13, wherein said power supply further comprises an adjustable low voltage DC regulator configured to drive a high voltage supply configured to provide input electrical power to said Blumlein transformer circuit.

19. The method of claim 13, wherein said insulated electrical antenna is configured to be any of a built-in furniture cushion or a user movable cushion.

20. The method of claim 13, wherein said electrical antenna is folds at least 2 feet/meters of an electrical conductor into a substantially flat circular or rectangular structure with an approximate surface area between 10 and 2,000 square inches.

* * * * *